United States Patent [19]

Fuchs

[11] Patent Number: 5,936,539
[45] Date of Patent: Aug. 10, 1999

[54] METHOD AND APPARATUS FOR AUTOMATIC CONFIGURATION OF A NETWORK NODE

[75] Inventor: Kenneth Fuchs, Wayland, Mass.

[73] Assignee: Siemens Medical Systems, Inc., Iselin, N.J.

[21] Appl. No.: 08/618,155

[22] Filed: Mar. 19, 1996

[51] Int. Cl.[6] .............................. G06F 3/00; G06F 17/00; H04Q 9/00
[52] U.S. Cl. ............................... 340/825.07; 340/825.06; 340/870.01; 340/825.49; 340/870.15; 340/825.36; 128/903; 455/95; 455/100
[58] Field of Search .................... 340/825.07, 825.49, 340/870.01, 870.15, 825.36, 825.08, 573; 128/903; 455/95, 100

[56] References Cited

U.S. PATENT DOCUMENTS

| | | | |
|---|---|---|---|
| 4,216,462 | 8/1980 | McGrath et al. | 340/150 |
| 4,804,950 | 2/1989 | Moon et al. | 340/715 |
| 4,916,441 | 4/1990 | Gombrich | 340/712 |
| 5,319,363 | 6/1994 | Welch et al. | 340/825.36 |
| 5,375,604 | 12/1994 | Kelly et al. | 128/671 |
| 5,534,851 | 7/1996 | Russek | 340/573 |
| 5,640,953 | 6/1997 | Bishop et al. | 128/630 |

FOREIGN PATENT DOCUMENTS

| | | |
|---|---|---|
| 0 261 927 | of 0000 | European Pat. Off. |
| 0 553 372 | of 0000 | European Pat. Off. |
| 0 735 498 | of 0000 | European Pat. Off. |
| 0 735 499 | of 0000 | European Pat. Off. |
| WO 93 01574 | of 0000 | WIPO |
| WO 94 24929 | of 0000 | WIPO |

*Primary Examiner*—William A. Cuchlinski, Jr.
*Assistant Examiner*—Yonel Beaulieu
*Attorney, Agent, or Firm*—Lawrence C. Edelman

[57] ABSTRACT

A monitor system of the type including at least one portable patient monitor for acquiring, processing and transferring patient data monitored from a patient, the system being distributed over at least two geographically separate patient monitoring areas which are interconnected via a communication network having a network node connection in each of the areas. A patient monitor docking station located in one of the patient monitoring areas provides for transmission of patient data from the portable patient monitor to the network via a selective coupling of the portable patient monitor to the network node connection. The docking station provides, in addition to the selective coupling to the portable monitor and apparatus for transferring patient data between the portable monitor and the docking station, a memory for storing network related information and transferring the network related information to the portable monitor when it is coupled to the docking station.

13 Claims, 3 Drawing Sheets

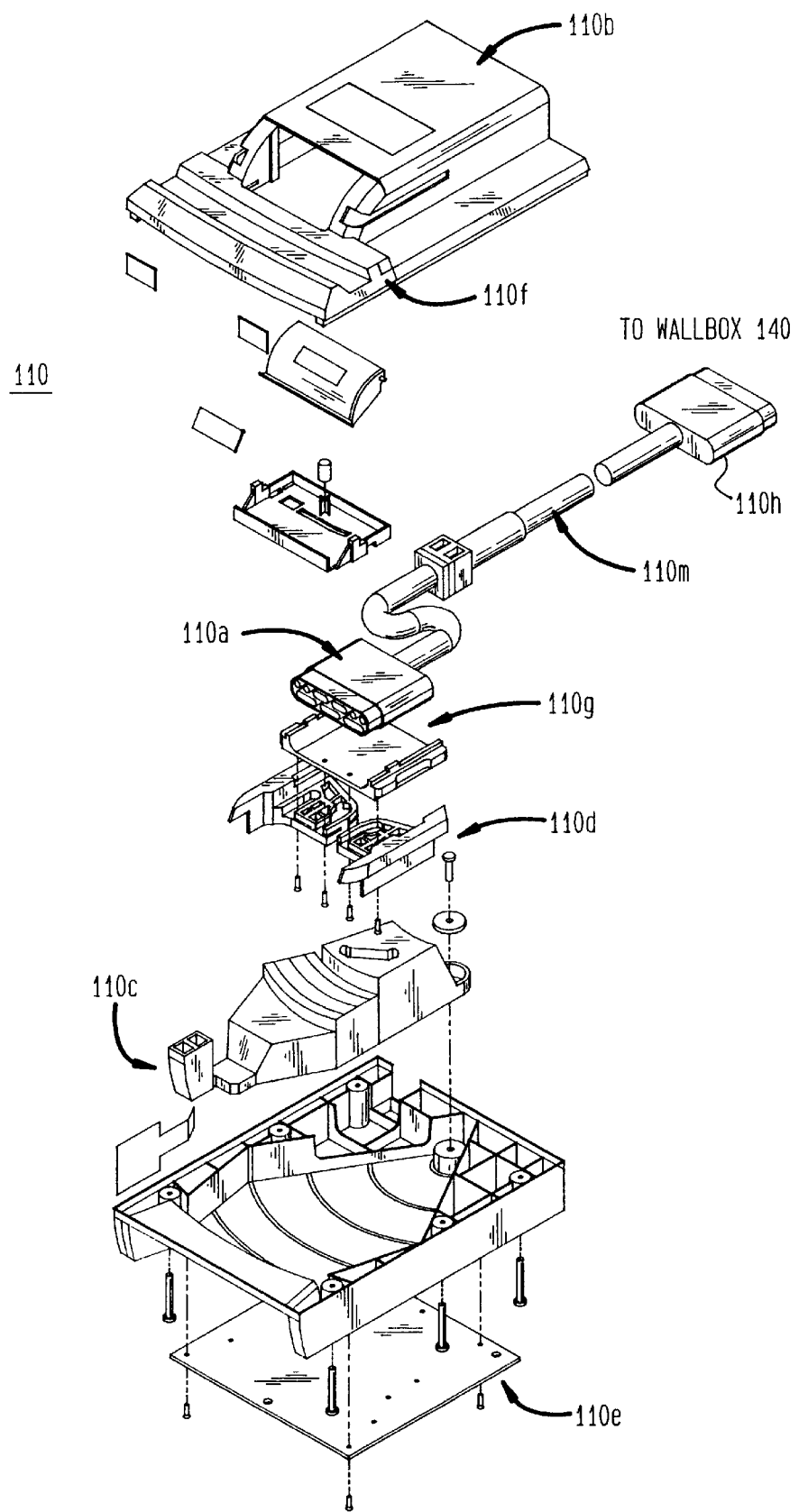

METHOD AND APPARATUS FOR AUTOMATIC CONFIGURATION OF A NETWORK NODE

FIELD OF THE INVENTION

The present invention relates to network systems, and in particular to a networked portable patient monitoring system for collecting, storing, and displaying medical data.

BACKGROUND OF THE INVENTION

In hospitals and other health care environments, it is often necessary to substantially continuously collect and analyze a variety of medical data from a patient. These data may include electrocardiogram, temperature, blood pressure, respiration, pulse and other parameters.

Patient monitoring systems have typically fallen into one of two general categories: multi-function monitoring, recording and displaying systems which process and collect all of the data desired, but are bulky and difficult to transport; and small, portable systems which are easy to transport, but process and collect fewer types of data and have limited storage capability.

The need for continuity of data collection and display is most pressing in emergency situations. During an emergency, the speed at which a patient is transferred from an ambulance to an emergency room, or from a bed to an operating room or intensive care unit may substantially impact the patient's chance of survival. Not only is it is important to provide a similar level of monitoring during transport as was provided during stationary applications, but it is also desirable from a clinical point of view to provide a substantially continuous monitoring capability and data history availability which follows the patient.

In accordance with the above desires, U.S. Pat. No. 5,375,604, entitled TRANSPORTABLE MODULAR PATIENT MONITOR, assigned to the same Assignee as the present invention, describes a transportable patient monitoring system of the type including at least two docking stations, one located at each of two geographically separated areas, both of which physically and electrically support a transportable patient monitor. Each docking station also provides a connection to a hospital communication network for transfer of patient related data between the portable monitor and the network.

Although the system described in the '604 patent is a vast improvement over the prior art, further improvement is desirable. For example, each patient care area is equipped with at least one node or connection point for connecting the docking station to the hospital network for allowing transfer of patient related information therebetween. Typically, a central monitoring or nurses station (or workstation) is also coupled to the node of the network for allowing a user (a nurse or physician) to monitor the patient from a remote location.

When a patient monitor is moved from one location in a hospital to another by transferring its connection from one docking station to another, it is important that certain aspects of its operation change with the change in its physical location. This is especially true of network-related configuration information. The conventional method of dealing with transported or relocated portable network devices is to manually reconfigure the networked device whenever it is moved. Information such as its Internet Protocol (IP) address, which is used by document printers, network servers, etc., are manually entered by a system administrator in order that the portable networked device can properly communicate with other devices connected to the network.

In a hospital setting, where it is the nurse that transports the patient, and moves the monitor with the patient, this is not an acceptable solution. Valuable time would be lost, errors in data entry could easily occur, and the nurse would be frustrated by having to deal with the equipment rather than the patient at a critical time.

It would be desirable to have a networked portable device in which the portable device can be easily disconnected from the network at one location and reconnected to the network at a different network location without requiring manual reconfiguration of the device with the network information of the new location.

Furthermore, it would be desirable that such easy disconnection for portable network devices be provided in a simple and cost effective manner.

It is an object of the present invention to provide such a network for portable devices, and specifically such a network for a portable patient monitoring system.

SUMMARY OF THE INVENTION

A monitor method and apparatus for acquiring, processing and displaying monitored data, for example physiological data acquired from at least one sensor adapted for attachment to a patient. The apparatus is distributed over at least two geographically separate monitoring areas via a communication network having at least one network node connection in each of the areas. A first part of the apparatus comprises a portable monitor for receiving and processing acquired data. A second part of the apparatus includes at least one monitor docking station in electrical communication with the communication network and located in at least one of the two monitoring areas for transmission of the monitored data between the portable monitor and the communication network. The docking station comprising a coupling means for facilitating a detachable coupling between the portable monitor to the docking station; signal transfer means for transferring patient related data signals between the portable monitor and the docking station when the portable monitor is coupled to the docking station; and a data storage means coupled to the signal transfer means for storing network related information therein, and transferring the network related information to the portable monitor when it is coupled to the docking station. In a preferred embodiment the portable monitor is a portable patient monitor in a networked patient monitoring system, and the network related information includes location specific address information of the node and identification of other devices connected to that node, as well as site specific monitor operation information.

BRIEF DESCRIPTION OF THE DRAWINGS

FIG. 3 illustrates an exploded view of the docking station platform shown in FIG. 2; and FIG. 4 illustrates in functional block diagram form portions of the monitor and docking station shown in FIG. 1, but in an alternative embodiment to that shown in FIG. 2.

DETAILED DESCRIPTION OF THE EXEMPLARY EMBODIMENT

Figure 1:
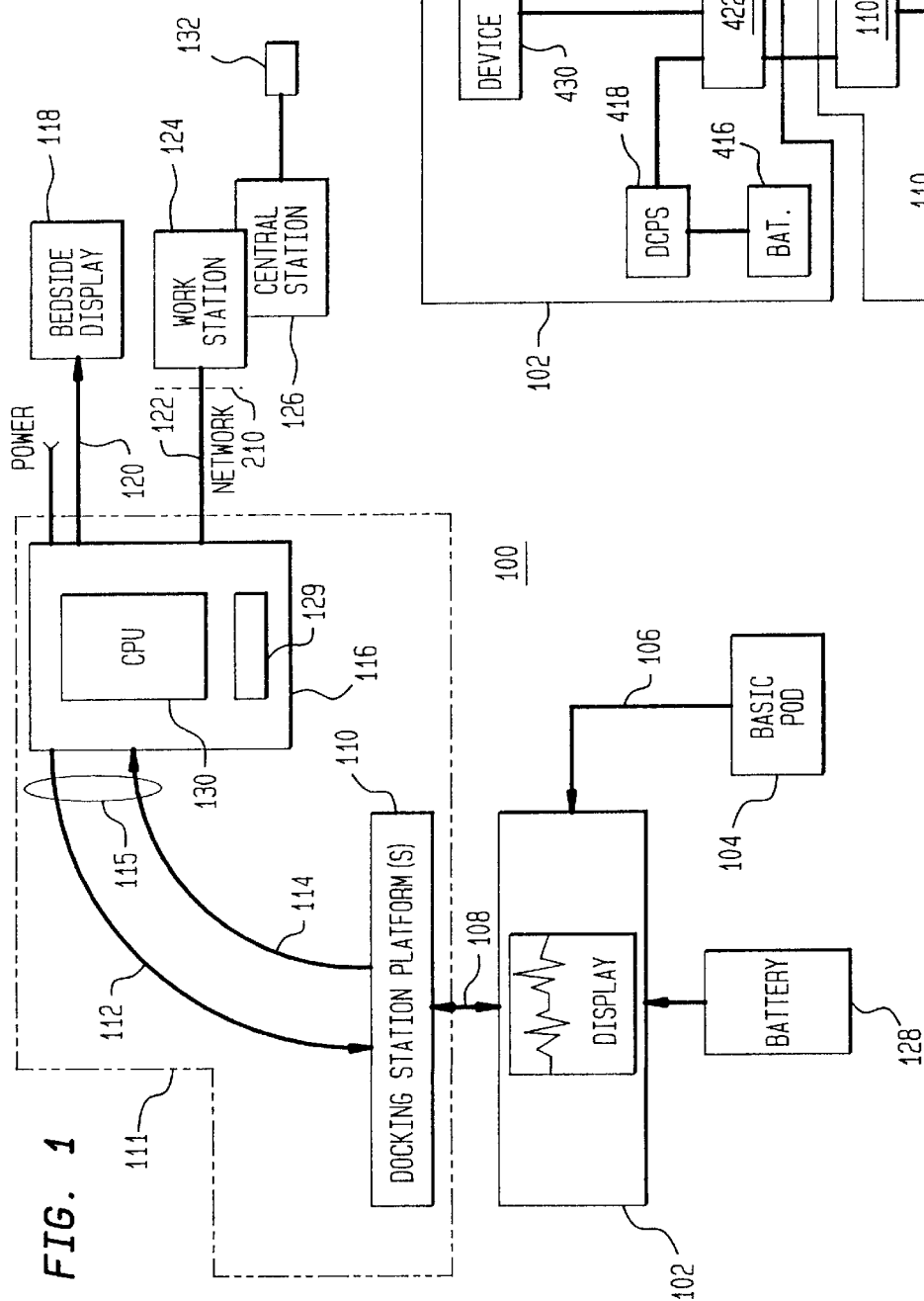
FIG. 1 illustrates in block diagram form a patient monitoring system constructed in accordance with the present invention.

FIG. 1 illustrates a networked portable monitoring system for connecting a portable monitor to a network in accordance with the present invention. In the exemplary embodiment the networked monitoring system 100 is a portable patient monitoring system, including a docking station 111 for connecting a portable patient monitor to a hospital patient information communication network. A portable monitor 102 acquires physiological data signals from a plurality of sensors (not specifically shown), which may include both invasive and non-invasive devices, for collecting physiological data from a patient. In the illustrated embodiment a basic pod 104 is provided in a housing remote from portable monitor 102 for acquiring, e.g., ECG, Sp 02 and Temperature data from a plurality of appropriate sensors connected to the patient, and providing this data to monitor 102 via a single detachable cable 106. Portable monitor 102 will typically display the physiological data, and also transmit patient-related data signals to docking station 111 via a connection 108. (It will be understood by one skilled in the art that the term "patient-related data", as used herein, may refer to the processed physiological information derived from the signals produced by sensors associated with pod 104, as well as signals for providing status, identification and control information to other devices in the monitoring system).

Docking station 111 provides power and communications services to portable monitor 102 during the time that monitor 102 is mounted on and in electrical communication with the docking station. The mounting mechanism, as will be described in detail later on, provides for rapid connection/disconnection of monitor 102 from docking station 111 (both mechanically and electrically) for transport. Preferably, the connection/disconnection is accomplished in a single step, so that the user can easily "pick-up and go" with monitor 102, easily and rapidly transporting it from a network connection node at one location to one at another location in the monitoring system, without handling any individual cables or connectors.

In the FIG. 1 embodiment, docking station 111 includes two modular components. The first component is a docking station platform 110. Portable monitor 102 may be placed on any one of a plurality of docking station platforms 110, which are typically distributed throughout the hospital in various patient care areas (Emergency room, ICU's CCU's etc.), and positioned, for example, near the patient's bed or attached to the bedframe. Docking station platform 110 provides both mechanical support for portable monitor 102, as well as electrical support, i,e., a connection 112 to a source of operating power and a connection 114 for transfer of acquired patient related data from portable monitor 102 to other networked devices. Connections 112 and 114 are typically included as part of a link or cable 115.

The second component of the docking station is a power supply and network box 116, referred to herein as wallbox 116, for completing the electrical connections provided by docking station platform 110. That is, wallbox 116 provides a source of operating power to connection 112 as well as providing for the transfer of the patient-related data acquired by monitor 102 to the other devices. Such transfer can comprise, e.g., a connection to a bedside display 118 via a direct connection 120, and a network connection (node) 122 for connection to a care unit network 210 (Local Area Network, LAN). Node 122 provides for transfer of the patient-related data to other devices connected to the network at other ones of the network nodes, such as a network connected intelligent workstation 124 or central station 126. Additional direct and network connections are possible for wallbox 116, but are not shown for the sake of brevity.

In the FIG. 1 embodiment, wallbox 116 is physically included in docking station 111. In an alternative embodiment shown in FIG. 2, wallbox 116 is referred to as a power supply and network box (PSN) 216, which is physically separate from docking station platform 110, and is coupled to docking station platform 110 via cable 115. In either embodiment, the functions provided by wallbox 116 and PSN 216 are very similar, and throughout the description this should be kept in mind. In either embodiment, wallbox 116 provides both power for operating monitor 102 (and for charging a battery pack 128 within, or attached to, monitor 102) and provides communications links to networks and devices, both inside and outside of the room in which docking station 111 is located. Furthermore, as will be described in detail later, in a further alternative embodiment shown in FIG. 6, docking station 111 only includes a low cost platform 110, and most of the functionality of wallbox 116 is included in the portable monitoring device. This results in a substantial simplification of platforms 110 which are normally located in each of the patient monitoring areas distributed throughout the hospital, thereby substantially reducing the cost of platforms 110, and hence the system cost.

Thus, docking station 111 provides a simple mechanism to connect portable monitoring devices with several other devices and networks without the need to connect individual cables for each device or network. Data and power connectors on the docking station platform 110 and on the cases of the portable devices allow simultaneous physical and electrical couplings to be established.

Portable monitor 102 is a self-contained, standalone monitoring device. Monitor 102 also includes all of the processing electronics necessary to process, display and store patient data during transport. In the exemplary embodiment described herein, portable monitor 102 does not include a broad suite of network interfaces; during transport, the exemplary monitor 102 does not have any connections to a central monitoring system or to communications networks, however wireless transmitting/receiving circuitry could be included in monitor 102 in order to provide network capability during transport.

As shown and described so far the system is substantially similar to the system shown and described in detail in Assignee's forenoted U.S. Pat. No. 5,375,604, incorporated herein by reference. For further details of this system, the reader should refer to this patent.

In accordance with the principles of the present invention docking station 111 includes a data storage means 129 for storing network related information therein, and coupled to connection 114 for transferring the network related information to the portable monitor when it is coupled to the docking station. The network related information includes location specific address information of the node (such as bed 2 at ICU 1, in workgroup 2), identification of other devices connected to that node (such as a networked display, printer, or workstation), as well as site specific monitor operation information. A network interface processor 130 is illustrated in the FIG. 1 embodiment, coupled at its input to the electrical connection 114 for monitoring the patient-related data signals provided by portable monitor 102, and has an output coupled to network node 122. Processor 130 comprises a central processing unit (CPU) and a memory 129 (ROM/RAM) which can access identity information of a portable monitor connected to docking station platform 110, and periodically (e.g., each 10 seconds) provides a name service (such as "monitor 56/bed 1/ICU 2") to node 122 for distribution to other devices on the network, such as workstation 124 and the central monitoring station 126, as well as a connection information signal indicative of the proper connection and/or proper removal or loss of signal from a portable monitor 102. This connection information signal is then communicated to the network along with the name service information for distribution to other devices on the network, such as the central monitoring station 126. In the event that connection information signal is indicative of an improper loss of signal or improper connection/disconnection of a portable monitor, where an alarm device 132 at central station 126 can be activated. Of course, if not monitor is connected to the docking station platform 110, only the node name service will be periodically sent onto the network.

More specifically, information to be included in data storage means 129 would include:

Internet Protocol (IP) address—an address required to support the TCP/IP protocol.

Monitoring Unit identification—this is used to denote a predetermined workgroup affiliation.

Node Number—to denote which node it is within the workgroup.

Bed Label'a user identifiable label, such as BED 1, WEST23, TELE14.

Care Unit Label'such as ICU, CCU, SICU, ER, OR, . . .

Hospital Label'name of hospital.

Remote Silence Enable'allow or disallow remote nodes to silence alarms.

Remote Control Enable'allow or disallow remote node to control portable device setup.

Recorder(s)'which recorder(s) should be used at this node

Printer(s)'which printer(s) should be used at this node.

Alarm Group'which alarm group does this node belong to

Recorder Label(s)'what is(are) the name of locally attached recorder(s)

Printer Label(s)'what is(are) the name of locally attached printer(s)

The above information can be transferred to storage device 129 by a system administrator during system set-up, as well known.

The docking station platform could also contain knowledge of the network related configuration information'this would include any network address information, logical node name, addresses of networked recorders or printers to be used, etc.

In operation, when a patient monitor 102 is attached to node 122, this information is immediately transferred to the monitor. The monitor uses this information to notify all attached nodes of its presence and status. Typically this information is incorporated in the header of its network transmissions, such as "NODE 122/CCU 3/UNIT 4/BED 2/ALL OK (or, MONITOR 56/with some patient related data, such as a portion of an EKG waveform)".

Figure 2:
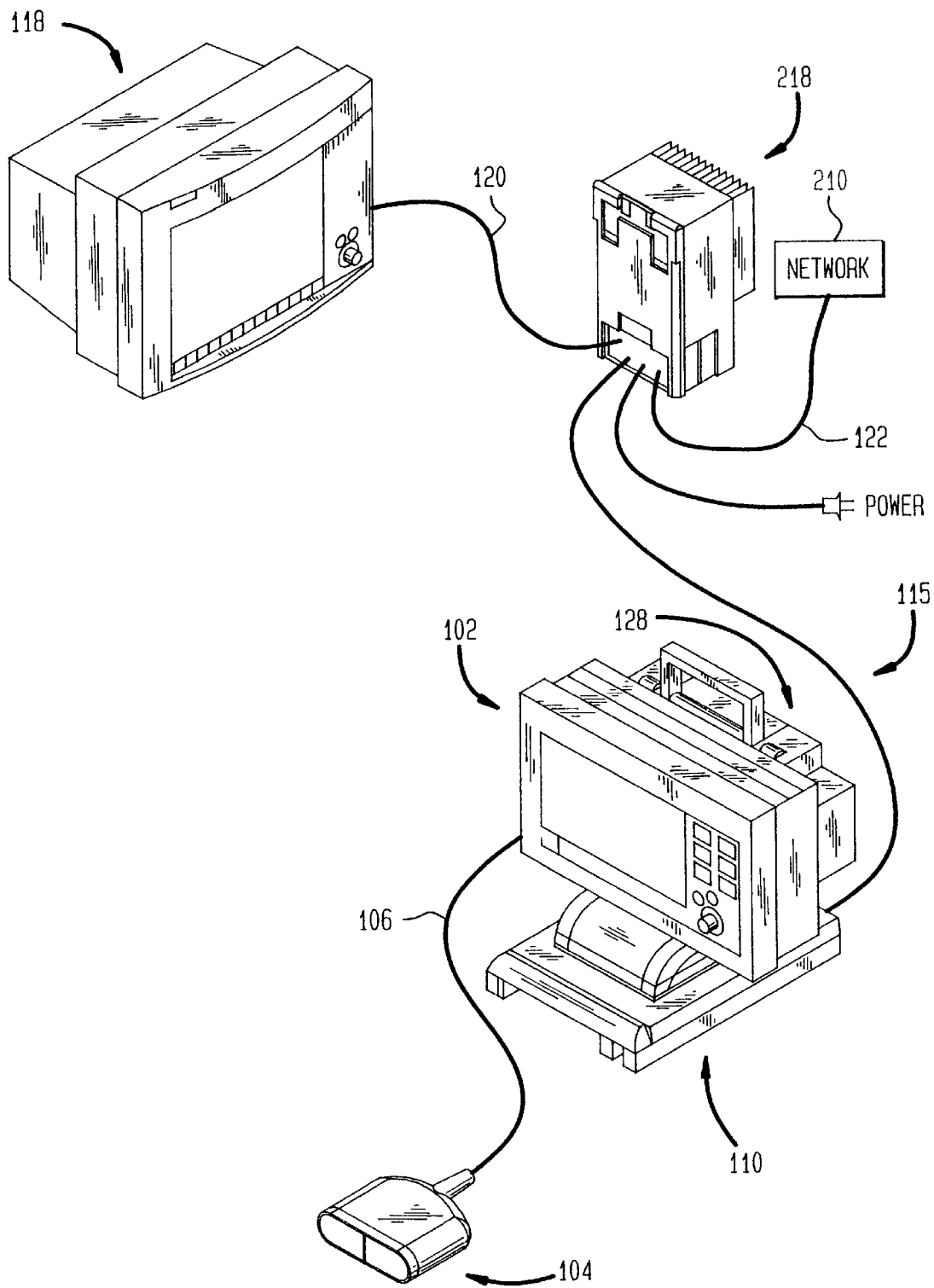
FIG. 2 illustrates an isometric view of the docking station platform and network connection wallbox shown in FIG. 1.

FIG. 2 shows an isometric view of an exemplary embodiment of the portable monitoring system 100 of FIG. 1, including a docking station platform 110, a PSN 216, a bedside display 118 and a network 210. Docking station platform 110 is connected to PSN 216 by one or more cables 115 (which provides the connections 112 and 114 shown in FIG. 1). Portable monitor 102 is mounted on docking station platform 110, providing physical support, power, and communications to other devices either directly and/or via a connection to node 122 of network 210. As previously noted, monitor 102 acquires physiological data signals from a data acquisition pod 104. Illustratively, pod 104 provides data from ECG, Spo2 and Temperature sensors connected to a patient (not shown). A battery pack 128 is shown attached to the rear portion of the case of portable monitor 102 for providing power to monitor 102 during transport. Note: although only a single docking station platform is shown in the illustrated patient monitoring area, multiple docking station platforms would be used to facilitate transport of a monitor device about the hospital in conjunction with movement of the patient. Thus, in a hospital or other health care facility, docking station platforms 110 will be distributed throughout the facility in geographically separate areas, yet they will all be connected to one another for transfer of patient data therebetween.

FIG. 3 shows an exploded view of an exemplary docking station platform 110 to which portable devices, such as portable monitors 102, may be attached. Cable 115 of FIG. 2 is shown as cable 110m, which carries electrical signals from PSN 216 to the portable monitor 102, through the docking station platform 110. A connector 110a at the docking station end of cable 110m is attached to a trolley 110g for controllable attachment to the portable device and a connector 110h at the other end of cable 110m interfaces with wallbox 116 using one of a variety of known LAN protocols.

A docking station top cover 110b not only functions as a protective cover, but also as a guide for mounting a portable device thereon. Cover 110b provides initial alignment using tapered outer edges and smooth rounded outer surfaces. Once aligned, contours along the outside top cover funnel the portable device into accurate final alignment, using positioning keys 110f. Keys 110f comprise one of more shaped indentation in the surface of top cover 110b and facilitate accurate alignment of a portable device with the docking station platform 110. Once positioned, flexible locking rail snaps 110d, flexibly protruding from the left and right sides on top cover 110b, fix the portable device to the docking station. Electrical connector 110a is then engaged with a corresponding electrical connector in the portable device by moving a lever arm 110c, which cams a docking station trolley 110g forward to mate with the corresponding connector in the portable device. The portable device is disengaged by moving lever arm 110c back to the initial position and release is accomplished by moving lever arm 110c an additional amount, using the reverse motion of its'camming action to retract the flexible locking rail snaps 110d from protruding from the sides of top cover 110b, thereby unlocking the portable device from docking station platform 110.

Many variations of the forenoted mechanical configuration are possible. For example, when mounting a docking station platform 110 to a bed or IV pole, both of which are movable, it is desirable to provide a fixed position wallbox 116 for coupling the docking station with power, devices and networks outside of the room in which the docking station is located. A PSN 216 mounted on a wall is suitable for this purpose. Furthermore, different technologies may be used to transmit data between portable monitor 102 and docking station 111. Examples of these technologies include infra red and radio frequency transmission techniques. It is understood by one skilled in the art that several such technologies are possible to be used with or as a replacement for the connection (cable 110m) between the portable monitor and network 210. Furthermore, although portable monitor 102 is shown to have a display, in an alternative embodiment it may not have a display and instead a remote display is used.

Finally, as previously noted, FIG. 4 illustrates in functional block diagram form portions of the monitor and docking station shown in FIG. 1, but in an alternative embodiment to that shown in FIG. 2. As shown in FIG. 4, docking station 111 is constructed as a low cost device, and as much functionality as possible is shifted to portable device 102. Therefore, the location of network signal processor 129 is shifted to the portable device, shown as network interface 430, and docking station 110 merely includes a data storage element, e.g., a non-volatile memory 429 (NVRAM), similar to memory 129 shown in FIG. 1, which stores the network related information therein. Memory 429 is preferably embodied as a removable EEPROM. On the other hand, monitor 102 also includes a non-volatile memory (NVRAM) 410 which contains default set-up and identification information provided by the manufacturer, as well as a battery backed-up memory (BRAM) 412 which contains the current monitor set-up information (monitor configurations and software licenses used by the monitor via its signal processor 430). Also shown as part of monitor 102 is a battery 416, a power supply 418, a user interface 420, and a docking station interface 422, for interfacing with a device interface 110a in docking station 110.

It is understood by one skilled in the art that many variations of the embodiments described herein are contemplated. While the invention has been described in terms of exemplary embodiments, it is contemplated that it may be practiced as outlined above with modifications within the spirit and scope of the appended claims.

I claim:

1. A monitor system for acquiring, processing and transferring monitored data from a patient, said system being distributed over at least two geographically separate patient monitoring areas and interconnected via a communication network having a network node connection in each of the areas, comprising:

a portable monitor for being coupled to the patient for receiving and processing patient data signals monitored therefrom; and at least one patient monitor docking station for being selectively coupled to the portable patient monitor, said at least one docking station being located in at least one of said patient monitoring areas, and connected for transmission of patient data received from the portable patient monitor to said network via one of said network node connections, wherein said docking station comprises:

coupling means for facilitating a detachable coupling between the portable monitor and the docking station;

signal transfer means for transferring patient-related data signals between the portable monitor and the docking station when the portable monitor is coupled to the docking station;

a data storage means coupled to the signal transfer means for storing network-related identity information therein, and transferring the network-related identity information, including location specific address information of said one network node connection, to the portable monitor when it is coupled to the docking station; and wherein said portable monitor incorporates said identity information into its transmission of patient related data signals from said portable patient monitor to said network via the signal transfer means of the docking station.

2. The system of claim 1 wherein the portable monitor comprises a portable patient monitor in a networked patient monitoring system.

3. The system of claim 1 wherein the network-related identity information transferred to the portable monitor comprises location specific address information of the network node connection and identification of other devices connected to that network node connection.

4. The system of claim 1, wherein said signal transfer means transfers said network-related identity information from said data storage means to said portable monitor upon initial coupling of said portable monitor to said docking station.

5. The system of claim 4, wherein said signal transfer means automatically transfers said network-related identity information from said data storage means to said portable monitor upon initial coupling of said portable monitor to said docking station.

6. The system of claim 1, wherein said data storage means comprises a non-volatile memory.

7. The system of claim 6, wherein said non-volatile memory comprises a removable electrically-erasable, programmable, read-only memory (EEPROM) loaded with said network-related identity information.

8. The system of claim 6, wherein said network-related identity information stored in said non-volatile memory comprises location information for the network node connection, including a network address, a work group affiliation and a bed location.

9. The system of claim 6, wherein said network-related identity information stored in said non-volatile memory comprises identification of auxiliary devices that are also connected to said network node connection.

10. The system of claim 6, wherein said network-related identity information stored in said non-volatile memory comprises information enabling/disabling network control of said portable monitor.

11. A method for operating a monitor system for acquiring, processing and transferring monitored data from a patient, said system being distributed over at least two geographically separate patient monitoring areas and interconnected via a communication network having a network node connection in each of the areas, said method comprising:

receiving and processing by a portable patient monitor patient data signals monitored from a patient; and selectively coupling the portable patient monitor to at least one docking station located in at least one of said patient monitoring areas, said docking station being connected for transmission of patient data received from the portable patient monitor to said network via one of said network node connections;

transferring patient-related data signals between the portable patient monitor and the docking station via a signal transfer means when the portable patient monitor is coupled to the docking station; and transferring network-related identity information to the portable patient monitor via data storage means coupled to the signal transfer means which stores therein the network-related identity information, including location specific address information of said one network node connection, when the portable patient monitor is coupled to the docking station.

12. The method of claim 11, wherein said step of transferring network-related identity information comprises transfer of said network-related identity information from said data storage means to said portable patient monitor upon initial coupling of said portable patient monitor to said docking station.

13. The method of claim 12, wherein said step of transferring network-related identity information comprises automatic transfer of said network-related identity information from said data storage means to said portable monitor upon initial coupling of said portable monitor to said docking station.

* * * * *